US008920673B2

(12) United States Patent
Del Sesto et al.

(10) Patent No.: US 8,920,673 B2
(45) Date of Patent: Dec. 30, 2014

(54) PHOSPHONIUM-BASED IONIC LIQUIDS AND USES

(75) Inventors: Rico E. Del Sesto, Los Alamos, NM (US); Andrew T. Koppisch, Flagstaff, AZ (US); Katherine S. Lovejoy, Santa Fe, NM (US); Geraldine M. Purdy, Chamita, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1028 days.

(21) Appl. No.: 12/958,693

(22) Filed: Dec. 2, 2010

(65) Prior Publication Data

US 2012/0138789 A1 Jun. 7, 2012

(51) Int. Cl.
| | |
|---|---|
| C07F 9/54 | (2006.01) |
| H01J 49/16 | (2006.01) |
| C07C 59/64 | (2006.01) |
| C07C 65/05 | (2006.01) |
| C07C 255/41 | (2006.01) |
| C07D 209/10 | (2006.01) |
| C07D 209/60 | (2006.01) |
| C07D 277/66 | (2006.01) |
| C07D 311/82 | (2006.01) |
| C07D 491/22 | (2006.01) |
| C09B 69/02 | (2006.01) |

(52) U.S. Cl.
CPC .............. *H01J 49/164* (2013.01); *C07C 59/64* (2013.01); *C07C 65/05* (2013.01); *C07C 255/41* (2013.01); *C07D 209/10* (2013.01); *C07D 209/60* (2013.01); *C07D 277/66* (2013.01); *C07D 311/82* (2013.01); *C07D 491/22* (2013.01); *C09B 69/02* (2013.01)
USPC ......................................... 252/182.12; 568/9

(58) Field of Classification Search
USPC ......................................... 252/182.12; 568/9
See application file for complete search history.

(56) References Cited

U.S. PATENT DOCUMENTS

| | | |
|---|---|---|
| 5,262,307 A | 11/1993 | Savolainen |
| 5,395,613 A | 3/1995 | Holland |

OTHER PUBLICATIONS

Rodriguez et al. "Ionic liquids for liquid-in-glass thermometers" Green Chemistry, 2008, vol. 10, pp. 501-507.*
Del Sesto, et al., "Tetraalkylphosphonium-based ionic liquids." J. Organomet. Chem., 2005, vol. 690, pp. 2536-2542.
Fraser, et al., "Phosphonium-based ionic liquids: an overview." Aust. J. Chem., Mar. 2009, vol. 62, pp. 309-321.
Crank, et al., "Towards a second generation of ionic liquid matrices (ILMs) for MALDI-MS of peptides, proteins, and carbohydrates." J. Am. Soc. Mass Spec., Jan. 2009, vol. 20, pp. 1790-1800.
Armstrong, et al., "Ionic liquids as matrixes for matrix-assisted laser desorption/ionization mass spectrometry." Anal. Chem., Aug. 2001, vol. 73, No. 15, pp. 3679-3686.
Tholey, et al., "Ionic (liquid) matrices for matrix-assisted laser desorption/ionization mass spectrometry—applications and perspectives." Anal. Bioanal. Chem., Jul. 2006, vol. 386, No. 1, pp. 24-37.
Ueki, et al., "Enhanced detection of sulfo-peptides as onium salts in matrix-assisted laser desorption/ionization time-of-flight mass spectrometry." Rapid Comm. Mass Spec., Mar. 2006, vol. 20, pp. 1615-1620.
Ueki, et al., "Analysis of acidic carbohydrates as their quaternary ammonium or phosphonium salts by matrix-assisted laser desorption/ionization mass spectrometry." Carb. Res., Jun. 2005, vol. 340, pp. 1722-1731.
Pei, et al., "Factors affecting ionic liquids based removal of anionic dyes from water." Environ. Sci. Technol., Jun. 2007, vol. 41, No. 14, pp. 5090-5095.
Han, et al., "Ionic liquids in separations." Acc. Chem. Res., 2007, vol. 40, No. 11, pp. 1079-1086.
Martak, et al., "Extraction of lactic acid by phosphonium ionic liquids." Sep. Purif. Technol., Feb. 2007, vol. 57, pp. 483-494.
Cytec Publication "Phosphonium-Based Ionic Liquids," 2009, pp. 1-20.
Gross, J.H., "Liquid Injection Field Desorption/Ionization-Mass Spectrometry of Ionic Liquids," J. Am. Soc. Mass Spectrom, 2007, vol. 18, pp. 2254-2262.

* cited by examiner

*Primary Examiner* — Joseph Kosack
(74) *Attorney, Agent, or Firm* — Samuel L. Borkowsky

(57) ABSTRACT

Phosphonium-based room temperature ionic liquids ("RTILs") were prepared. They were used as matrices for Matrix-Assisted Laser Desorption Ionization (MALDI) mass spectrometry and also for preparing samples of dyes for analysis.

10 Claims, No Drawings

PHOSPHONIUM-BASED IONIC LIQUIDS AND USES

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to phosphonium-based room temperature ionic liquids ("RTILs) and more particularly to phosphonium-based RTILs for matricies for matrix-assisted laser desorption ionization ("MALDI") mass spectrometry and for extraction.

BACKGROUND OF THE INVENTION

Phosphonium-based room temperature ionic liquids ("RTILs") are molten salts with a melting temperature below 100° C. (see, for example, Del Sesto et al, "Tetraalkylphosphonium-based Ionic Liquids," J. Organomet. Chem., 2005, vol. 690, pp. 2536-2542, and Fraser et al., "Phosphonium-Based Ionic Liquids: An Overview," Aust. J. Chem., 2009, vol. 62, pp. 309-321, both incorporated by reference herein). They resist oxidation and reduction over a wide voltage range. They are recyclable. They are typically less dense than water. They tend to be more thermally stable and less expensive than nitrogen-based RTILs. Many are commercially available. Phosphonium-based RTILs have been used for a variety of applications including phase transfer catalysis, hydroformylation, carbonylation, liquid-liquid extraction, and some aspects of mass spectrometry. Little is known about phosphonium-based RTILs as matrices in matrix-assisted laser desorption ionization ("MALDI") mass spectrometry.

SUMMARY OF THE INVENTION

In accordance with the purposes of the present invention, as embodied and broadly described herein, an aspect of the present invention includes a matrix-assisted laser desorption ionization mass spectrometry. The matrix includes a composition of the formula $[PR_4]_m[X]_n$ that is a molten salt with a melting temperature below 100° C. Each R is a group that includes 4-22 carbons, m is 1 or 2, and n is 1. Each R is independently selected from alkyl, alkenyl, alkynyl, phenyl, and aryl. X is an anion selected from 2,5-dihydroxybenzoate, α-cyano-4-hydroxycinnamate, ferulate, and a dye anion.

Another aspect of the present invention is a kit for preparing a sample of a soluble analyte in a matrix for analysis by matrix-assisted laser desorption ionization mass spectrometry. The kit includes a compound of the formula $[PR_4]_m[X]_n$ wherein m is 1 or 2, wherein n is 1, wherein each R is a group that comprises 4-22 carbons and is independently selected from alkyl, alkenyl, alkynyl, phenyl, and aryl, wherein X is an anion selected from 2,5-dihydroxybenzoate, α-cyano-4-hydroxycinnamate, ferulate, and a dye anion, the dye anion selected from

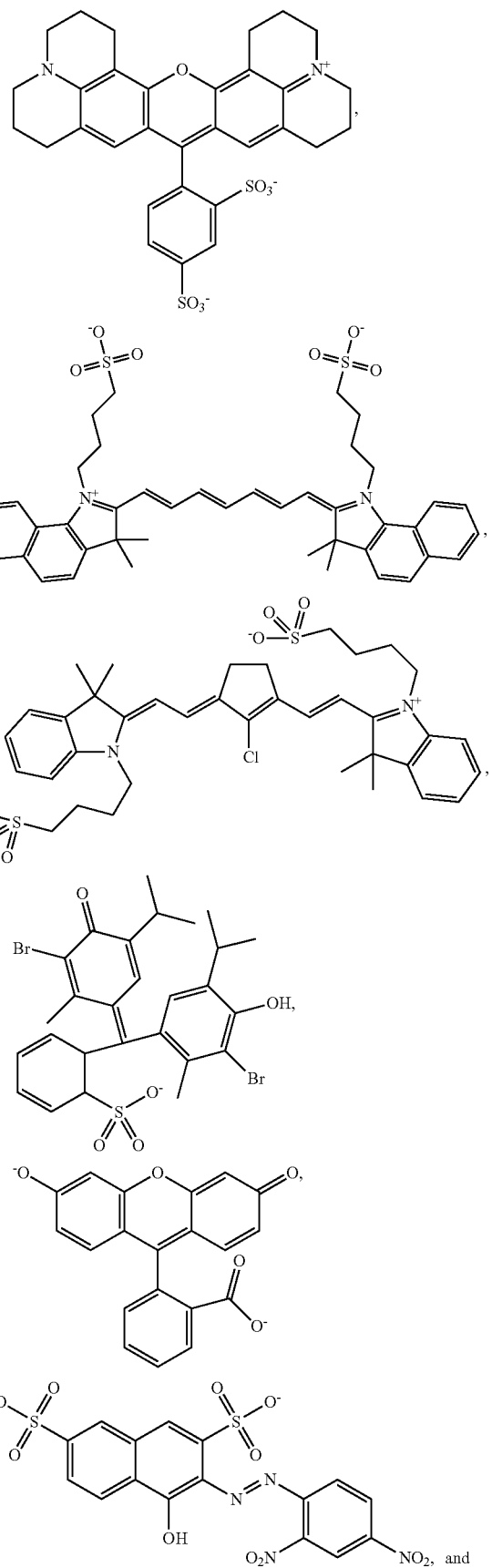

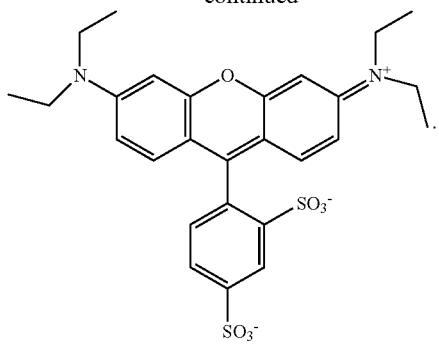

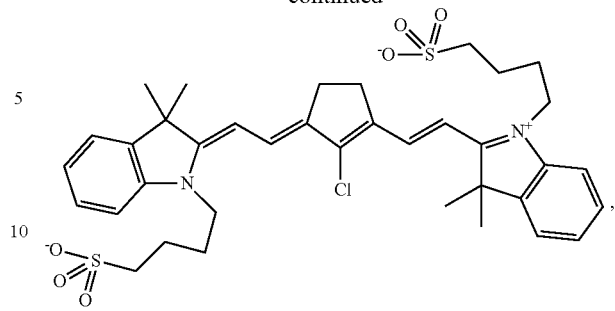

The kit also includes instructions for preparing a sample of a soluble analyte in a matrix for analysis by matrix-assisted laser desorption ionization mass spectrometry, wherein the matrix for the analysis is the above compound.

Another aspect of the present invention relates to a method for analyzing a dye from a keratinous substrate using matrix-assisted laser desorption ionization mass spectrometry. According to the method a keratinous substrate with a dye attached to the keratinous substrate is provided. The keratinous substrate with attached dye is subjected to conditions resulting in denaturing of the keratinous substrate, which separates the dye from the substrate. The dye is dissolved in a phosphonium-based ionic liquid suitable as a matrix for matrix-assisted laser desorption ionization mass spectrometry. Then, the solution of the dye is analyzed by matrix-assisted laser desorption mass spectrometry.

Yet another aspect of the invention relates to a composition of the formula $[PR_4]_m[X]_n$ wherein m is 1 or 2, wherein n is 1, wherein each R is a group that comprises 4-22 carbons and is independently selected from alkyl, alkenyl, alkynyl, phenyl, and aryl, wherein X is an anion selected from 2,5-dihydroxybenzoate, α-cyano-4-hydroxycinnamate, ferulate, and a dye anion. The dye anion is selected from

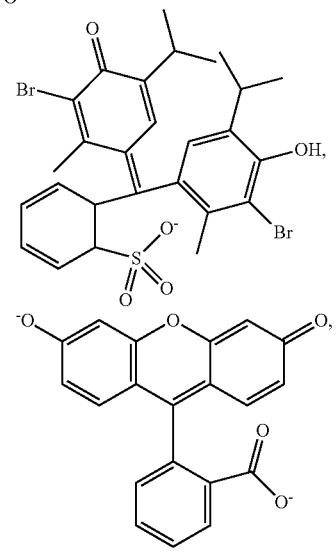

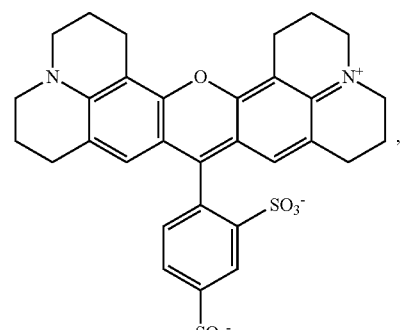

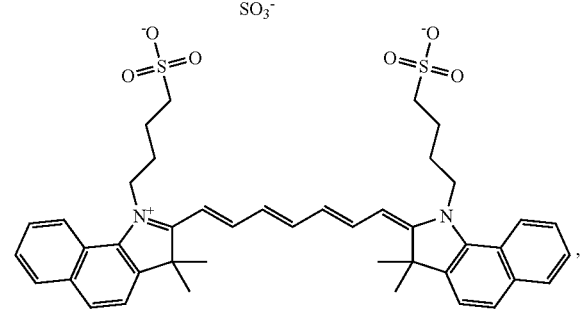

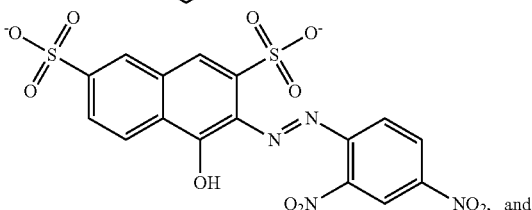

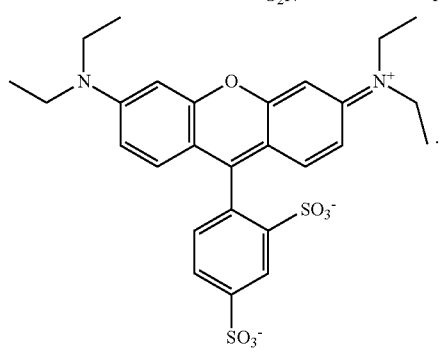

Another aspect of the invention is concerned with a composition of the formula $[PR_4]_m[X]_n$ wherein m is 1 or 2, wherein n is 1, wherein each R is a group that comprises 4-22 carbons, wherein each R is independently selected from linear alkyl, branched alkyl, cycloalkyl, linear alkenyl, branched alkenyl, cycloalkenyl, phenyl, aryl, linear alkynyl, and branched alkynyl, wherein X is selected from all-trans-retinoate, iodate, anthraquinone-2-carboxylate, 7-hydroxycoumarinyl-4-acetate, aurintricarboxylate, 3,6-dihydroxyflavone, 9-hydroxy-9-fluorenecarboxylate, 2-(4-hydroxyphenylazo)benzoate, mellitate, 2,3-napthalenedicarboxylate, sinapate, succinate, 2-(4- hydroxyphenylazo)benzoate, caffeate (3,4-dihydroxycinnamate), nicotinate, anthranilate, trans-3-indoleacrylate, picolinate, or 3-hydroxypicolinate, said composition having a melting temperature of less than 100° C.

Another aspect of the invention relates to a method for preparing a dye-containing sample for analysis. According to the method, a solution of a dye is provided. Also provided is a composition of the formula $[PR_4]_m[X]_n$ wherein m is 1 or 2, wherein n is 1, wherein each R is a group that comprises 4-22 carbons and is independently selected from alkyl, alkenyl, alkenyl, phenyl, and aryl, wherein X is an anion selected from chloride, bromide, iodide, hydroxide, acetate, tetrafluoroborate, dicyanamide, bis(trifluoromethanesulfonyl)amide, tosylate, carboxylate, phosphinate, dialkylphosphate, phosphate, methylcarbonate, decanoate, 2-ethylhexanoate, bis(2,4,4-trimethylpentyl)phosphinate, dodecylsulfonate, methanesulfonate, glycolate, diisobutylmonothiophosphate, diisobutyldithiophosphate, benzoate, tridecylsulfosuccinate, alkylsulfate, 2,5-dihydroxybenzoate, α-cyano-4-hydroxycinnamate, ferulate, sinapate, succinate, 2-(4-hydroxyphenylazo)benzoate, caffeate, nicotinate, anthranilate, trans-3-indoleacrylate, picolinate, 3-hydroxypicolinate, 2,5-dihydroxybenzoate, α-cyano-4-hydroxycinnamate, and ferulate. The solution and the composition are contacted, whereupon the dye is extracted from solution and into the composition, thus preparing a dye-containing sample for analysis.

DETAILED DESCRIPTION

This invention is concerned with these aprotic phosphonium-based room temperature ionic liquids ("RTILs").

An aspect of the invention is concerned with phosphonium-based RTILs as matrices for matrix-assisted laser desorption ionization ("MALDI") mass spectrometry for a variety of soluble analytes including cationic, anionic, and neutral analytes. Small soluble molecules may be analytes. The matrix is a molten salt with a melting temperature below 100° C., and includes a composition of the formula $[PR_4]_m[X]_n$ wherein m is 1 or 2, wherein n is 1. Each R is a group that includes 4-22 carbons and each R is independently selected from alkyl (linear, branched, cycloalkyl), alkenyl (linear, branched, cycloalkenyl), phenyl, and aryl. X is an anion selected from 2,5-dihydroxybenzoate, α-cyano-4-hydroxycinnamate, ferulate, and dye anions. Examples of dye anions include, but are not limited to, those having the following structural formulas:

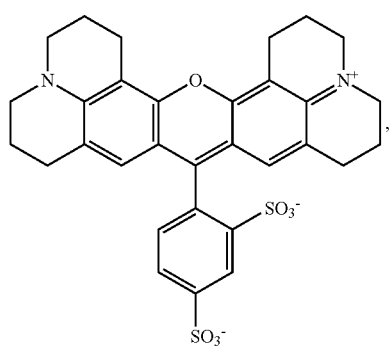

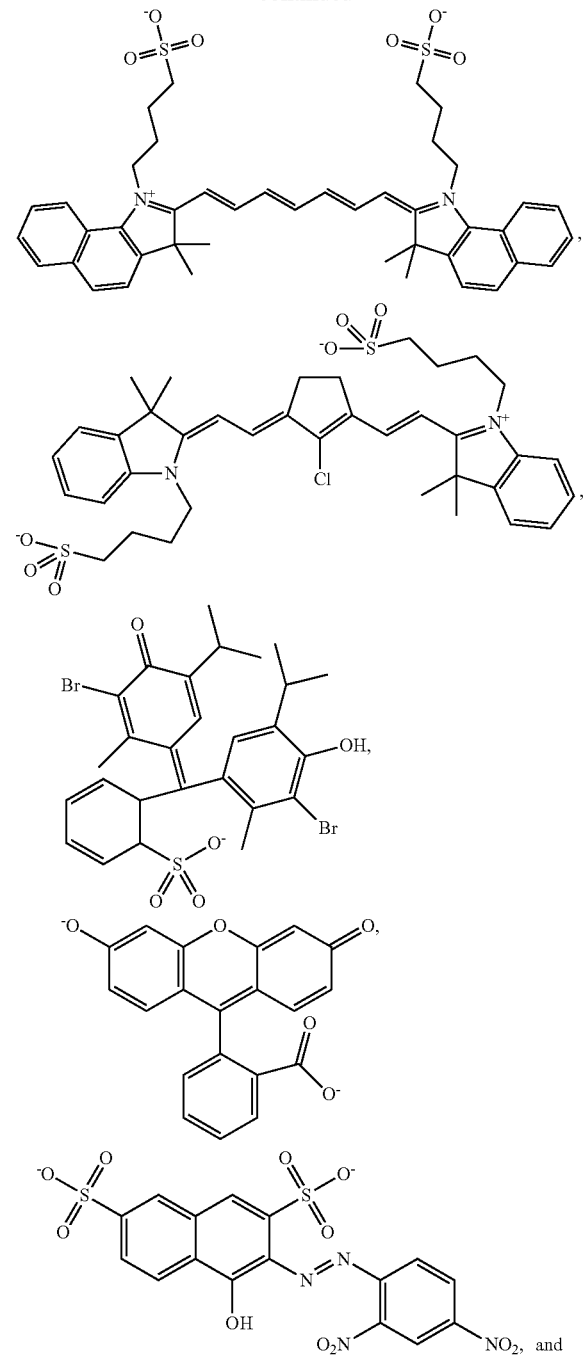

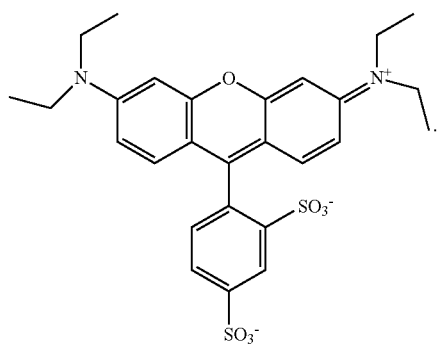

Embodiment [PR$_4$] cations include, but are not limited to, trihexyltetradecylphosphonium, triisobutyl(methyl)phosphonium, tributyl(methyl)phosphonium, tributyl(hexadecyl)phosphonium, tetrabutylphosphonium, tetraoctylphosphonium, tetradecyl(tributyl)phosphonium, ethyl(tributyl)phosphonium), tributyl(methyl)phosphonium, triisobutyl(methyl)phosphonium, triisobutyl(ethyl)phosphonium, triethyl(methoxyethyl)phosphonium, tri(isobutyl)methylphosphonium, triethyl[2-(2-methoxyethoxy)ethyl]phosphonium, tetraphenylphosphonium, butyltriphenylphosphonium, trihexylmethylphosphonium, and trihexyl(ethyl)phosphonium.

Other compositions that are expected to be useful as matrices for MALDI mass spectrometry include the above PR$_4$ cations (i.e. trihexyltetradecylphosphonium, triisobutyl(methyl)phosphonium, tributyl(methyl)phosphonium, tributyl(hexadecyl)phosphonium, tetrabutylphosphonium, etc.) and X anions selected from all-trans-retinoate, iodate, anthraquinone-2-carboxylate, 7-hydroxycoumarinyl-4-acetate, aurintricarboxylate, 3,6-dihydroxyflavone, 9-hydroxy-9-fluorenecarboxylate, 2-(4-hydroxyphenylazo)benzoate, mellitate, 2,3-napthalenedicarboxylate, sinapate, succinate, 2-(4-hydroxyphenylazo)benzoate, 3,4-dihydroxycinnamate, nicotinate, anthranilate, trans-3-indoleacrylate, picolinate, 3-hydroxypicolinate, chloride, bromide, iodide, hydroxide, acetate, an anionic dye, tetrafluoroborate, dicyanamide, bis(trifluoromethanesulfonyl)amide, tosylate, carboxylate, phosphinate, dialkylphosphate, phosphate, methylcarbonate, decanoate, 2-ethylhexanoate, bis(2,4,4-trimethylpentyl)phosphinate, dodecylsulfonate, methanesulfonate, glycolate, diisobutylmonothiophosphate, diisobutyldithiophosphate, benzoate, tridecylsulfosuccinate, and alkylsulfate.

Phosphonium-based RTILs were prepared that included a conjugate base of a compound that has been used in the past as a solid matrix for MALDI mass spectrometry. For example, the embodiment phosphonium-based RTIL trihexyltetradecylphosphonium 2,5-dihydroxybenzoate was prepared and shown to be a matrix for MALDI mass spectrometry. 2,5-dihydroxybenzoate ("DHB") is the conjugate base of 2,5-dihydroxybenzoic acid ("DHBH"), which is a known matrix material for MALDI mass spectrometry. Other embodiment phosphonium-based RTILs that were prepared and shown to be matrices for MALDI mass spectrometry include trihexyltetradecylphosphonium α-cyano-4-hydroxycinnamate and trihexyltetradecyl ferulate. The anion α-cyano-4-hydroxycinnamate ("CHCA") is the conjugate base of α-cyano-4-hydroxycinnamic acid ("CHCAH"), which is a known matrix for MALDI. In the other, ferulate ("FA") is the conjugate base of ferulic acid ("FAH"), which is also a known matrix for MALDI.

The properties of [trihexylphosphonium][X] where X is DHB, CHCA, or FA were compared to those of trihexyltetradecylphosphonium chloride and also to DHBH, CHCAH, and FAH. Ionization efficiencies of analytes were calculated; they compare well with the ionization efficiencies of the analytes using trihexyltetradecylphosphonium chloride. They also compare well with the ionization efficiencies of the analytes using DHBH, CHCAH, and FAH, which are known matricies for MALDI mass spectrometry.

The solid matrix compounds DHBH, CHCAH, and FAH are known to absorb at a MALDI laser wavelength of 337 nanometers. Prior to their synthesis, it was hoped that trihexyltetradecylphosphonium DHB, CHCA, and FA would also absorb at this wavelength. After synthesizing the embodiment RTILs, it was found that all three did absorb at 337 nanometers. It was also found that the UV-Vis absorption spectrum of trihexyltetradecylphosphonium DHB was similar to the UV-VIS absorption spectrum of DHBH. Similarly, it was found that the absorption spectra for trihexyltetradecylphosphonium CHCA and FA were similar to the spectra for CHCAH and FAH, respectively.

In the preparation of trihexyltetradecylphosphonium 2,5-dihydroxybenzoate (Example 1, vide infra), if the pH of the reaction was not controlled, then the ratio of PR$_4$:DHB for the ion exchange (chloride exchanged for DUB) was actually close to 2:1. A pH of approximately 7 was found to be optimal for driving the DHB exchange to 97% substitution. At pH 7, the monoanionic form of DHB (pKa1=2.77, pKa2=10.01) is present.

In the preparation of trihexyltetradecylphosphonium α-cyano-4-hydroxycinnamate from trihexyltetradecylphosphonium chloride, is was found that CHCA could also be driven to high substitution (99%) for chloride at pH 6.5 (pKa1=2.62, pKa2=7.93). The anion is not soluble in dichloromethane as the sodium salt, but is extracted into the organic phase due to the presence of the ionic liquid.

Other preparations of embodiment ionic liquids having an anion that is the conjugate base of a known solid matrix for MALDI involve a one-phase methanolic synthesis that depends on proton exchange between a Bronstead acid and base. The two-phase procedure was preferred for limiting the amount of anion extracted into the organic/ionic liquid phase to adjust the amount for charge balance and to promote a 1:1 PR$_4$:anion stoichiometry. Additionally, protic ionic liquids prepared in the one-phase procedure may contain neutral species that result from proton transfer.

A factor in driving the anion exchange was the volume of the organic layer. This may indicate that the [PR$_4$][X] RTILs where the anion X is a conjugate base of the solid matrix acids are not as soluble as trihexyltetradecylphosphonium chloride is in dichloromethane. An organic layer volume of 200 milliliters was found to be suitable for preparation of the ionic liquids on a scale using 13 millimoles of the anion.

The following non-limiting Examples describe preparations of embodiment RTILs that were shown to be useful as matricies for MALDI mass spectrometry. Trihexyltetradecylphosphonium chloride was obtained from CYTEC INDUSTRIES, Inc. under the trade name CYPHOS101. Prior to its use in a synthesis, CYPHOS101 was purified by (a) washing with water, (b) extracting with hexanes until the UV-VIS absorption beyond 350 nm disappeared, and (c) drying under a vacuum at 90° C. UV-Vis absorption spectra were collected on a HEWLETT-PACKARD 8453 diode array spectrophotometer in a 1 cm path length quartz cuvette. DHBH was obtained from ALDRICH CHEMICAL COMPANY. CHCAH was obtained from ACROS ORGANICS. FAH was obtained from MP BIOMEDICALS INC. In the RTIL examples 4-12, the anion portion is a dye anion. The chemical names and structural formulas for each embodiment RTIL are provided.

EXAMPLE 1

Preparation of trihexyltetradecylphosphonium 2,5-dihydroxybenzoate

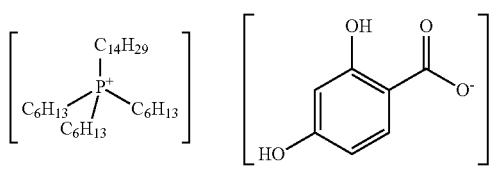

To 100 milliliters of an aqueous solution of 2,5-dihydroxybenzoic acid (2.0 grams, 13 millimoles) in water was added a 0.2 M solution of sodium bicarbonate until the pH of the solution was 6.5. The solution was stirred for 30 minutes until gas evolution ceased. Dichloromethane (50 milliliters) was added, followed by a solution of trihexyltetradecylphosphonium chloride (3.1 grams, 6 millimoles) in 150 milliliters of dichloromethane. The two layers were stirred vigorously for 24 hours. The organic layer was removed and washed with water. The solvent was evaporated. Heating at 80° C. under a vacuum yielded dry trihexyltetradecylphosphonium 2,5-dihydroxybenzoate.

EXAMPLE 2

Preparation of trihexyltetradecylphosphonium α-cyano-4-hydroxycinnamate

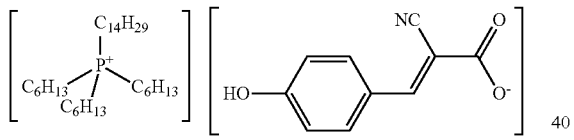

To 100 milliliters of an aqueous solution of α-cyano-4-hydroxycinnamic acid (2.0 grams, 11 millimoles) in water was added a 0.2 M solution of sodium bicarbonate until the pH of the solution was 6.5. The solution was stirred for 30 minutes until gas evolution ceased. Dichloromethane (50 milliliters) was added, followed by a solution of trihexyltetradecylphosphonium chloride (2.5 grams, 4.8 millimoles) in 150 milliliters of dichloromethane. The two layers were stirred vigorously for 24 hours. The organic layer was removed and washed with water. The solvent was evaporated. Heating at dried at 80° C. under a vacuum yielded dry trihexyltetradecylphosphonium α-cyano-4-hydroxycinnamate.

EXAMPLE 3

Preparation of trihexyltetradecylphosphonium ferulate

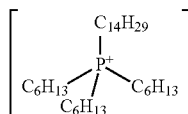

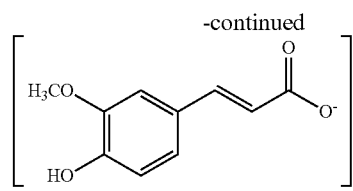

To 100 milliliters of an aqueous solution of ferulic acid (2.0 grams, 10 millimoles) in water was added a 0.2 M solution of sodium bicarbonate until the pH of the solution was 6.5. The solution was stirred for 30 minutes until gas evolution ceased. Dichloromethane (50 milliliters) was added, followed by a solution of trihexyltetradecylphosphonium chloride (2.5 grams, 4.8 millimoles) in 150 milliliters of dichloromethane. The two layers were stirred vigorously for 24 hours. The organic layer was removed and washed with water. The solvent was evaporated. Heating at 80° C. under a vacuum yielded dry trihexyltetradecylphosphonium ferulate.

EXAMPLE 4

Preparation of 2',3',6',7',12',13',16',17'-octahydro-spiro[3H-2,1-benzoxathiole-3,9'-[1H,5H,9H,11H,15H]xantheno[2,3,4-ij:5,6,7-i'j']diquinolizine]-6-sulfonic acid, 1,1-dioxide, trihexyltetradecylphosphonium salt

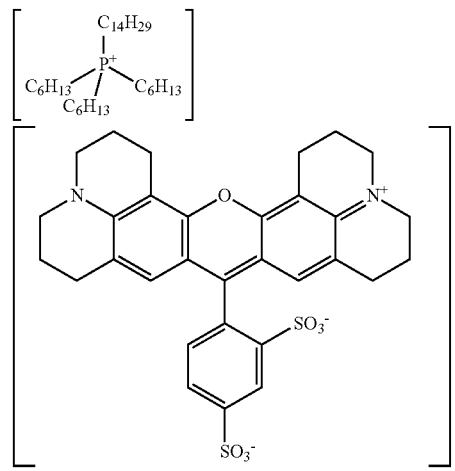

2.5 grams (4.0 millimoles) of 2',3',6',7',12',13',16',17'-octahydro-spiro[3H-2,1-benzoxathiole-3,9'-[1H,5H,9H,11H,15H]xantheno[2,3,4-ij:5,6,7-i'j']diquinolizine]-6-sulfonate, 1,1-dioxide, sodium salt (also known as SULFORHODAMINE 640) was dissolved in 200 ml of deionized water. Trihexyltetradecylphosphonium chloride (4.27 grams, 8.2 millimoles) was dissolved in 200 ml dichloromethane. The two solutions were combined into a round bottom flask and stirred for 48 hours. The mixture was transferred to a separatory funnel. The organic phase was separated from the aqueous phase. The organic phase was placed back into the separatory funnel and washed with 200 ml deionized water. The organic phase was collected and rotovapped to remove the solvent, and the ionic liquid product 2',3',6',7',12',13',16',17',-octahydro-spiro[3H-2,1-benzoxathiole-3,9'-[1H,5H,9H,11H,15H]xantheno[2,3,4-ij:5,6,7-i'j']diquinolizine]-6-sulfonic acid, 1,1-dioxide, trihexyltetradecylphosphonium salt was collected.

EXAMPLE 5

Preparation of 4-(2-{7-[1,1-dimethyl-3-(4-sulfo-butyl)-1H-benzo[E]indol-2-yl]-hepta-2,4,6-trienylidene}-1,1-dimethyl-benzo[E]indolium-3-yl)-butane-1-sulfonic acid trihexyltetradecylphosphonium salt

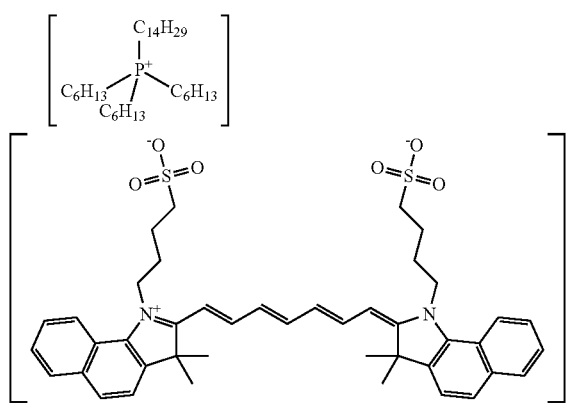

A solution of 4-(2-{7-[1,1-dimethyl-3-(4-sulfo-butyl)-1H-benzo[E]indol-2-yl]-hepta-2,4,6-trienylidene}-1,1-dimethyl-benzo[E]indolium-3-yl)-butane-1-sulfonate sodium salt (otherwise known in the art as INDOCYANINE GREEN or "IR 125") (2.5 grams, 3.2 millimoles) in 200 ml methanol was prepared. A solution of trihexyltetradecylphosphonium chloride (3.32 grams, 6.4 millimoles) 200 ml methanol was also prepared. The two solutions were combined in a round bottom flask and stirred for 24 hours. Dichloromethane (80 ml) was added to the mixture, and the mixture was observed for separation, but no separation was observed. The mixture was rotovapped, after which 200 ml of dichloromethane and 100 ml of deionized water were added. The mixture was stirred overnight, and then transferred to a separatory funnel where the organic phase was separated from the aqueous phase. The organic phase was washed with 200 ml deionized water, and then rotovapped, leaving the ionic liquid product 4-(2-{7-[1,1-Dimethyl-3-(4-sulfo-butyl)-1H-benzo[E]indol-2-yl]-hepta-2,4,6-trienylidene}-1,1-dimethyl-benzo[E]indolium-3-yl)-butane-1-sulfonic acid trihexyltetradecylphosphonium salt, which was collected.

EXAMPLE 6

Preparation of 2-[2-[2-chloro-3-[2-[1,3-dihydro-3,3-dimethyl-1-(4-sulfobutyl)-2H-indol-2-ylidene]-ethylidene]-1-cyclopenten-1-yl]-ethenyl]-3,3-dimethyl-1-(4-sulfobutyl)-3H-indolium, inner salt trihexyltetradecylphosphonium salt

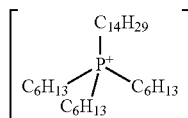

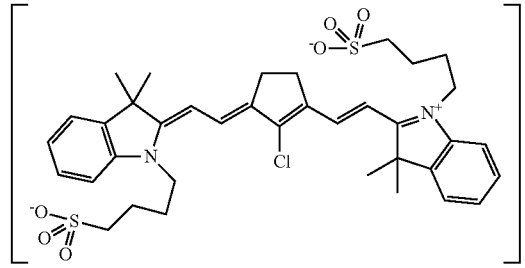

An amount of 0.5 grams (0.7 millimoles) of the dye known as IR 806 (i.e. 2-[2-[2-chloro-3-[2-[1,3-dihydro-3,3-dimethyl-1-(4-sulfobutyl)-2H-indol-2-ylidene]-ethylidene]-1-cyclopenten-1-yl]-ethenyl]-3,3-dimethyl-1-(4-sulfobutyl)-3H-indolium hydroxide, inner salt sodium salt) was dissolved in 50 ml deionized water. A solution of trihexyltetradecylphosphonium chloride (0.374 grams, 0.7 millimoles) in dichloromethane (50 ml) was prepared. The two solutions were combined into a round bottom flask and stirred for 24 hours. The mixture was transferred to a separatory funnel where the organic phase was separated from the aqueous phase, then washed with 50 ml deionized water, and then rotovapped, leaving the ionic liquid product 2-[2-[2-chloro-3-[2-[1,3-dihydro-3,3-dimethyl-1-(4-sulfobutyl)-2H-indol-2-ylidene]-ethylidene]-1-cyclopenten-1-yl]-ethenyl]-3,3-dimethyl-1-(4-sulfobutyl)-3H-indolium, inner salt trihexyltetradecylphosphonium salt, which was collected.

EXAMPLE 7

Preparation of trihexyltetradecylphosphonium salt of 4,4'-(1,1-dioxido-3H-2,1-benzoxathiole-3,3-diyl)bis(2-bromo-6-isopropyl-3-methylphenol)

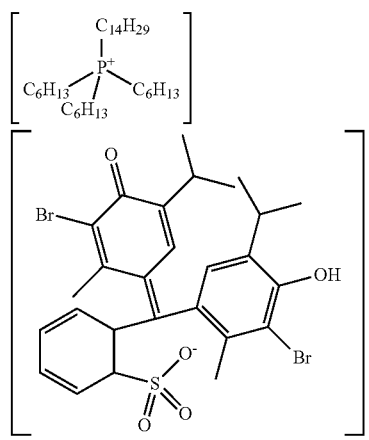

A solution of 4,4'-(1,1-dioxido-3H-2,1-benzoxathiole-3,3-diyl)bis(2-bromo-6-isopropyl-3-methylphenol (otherwise known as "bromothymol blue") (2.5 grams, 3.9 millimoles), in deionized water (200 ml) was prepared. A solution of trihexyltetradecylphosphonium chloride (0.2 grams, 3.9 millimoles) was in 200 ml dichloromethane was also prepared. The two solutions were combined in a round bottom flask and stirred for 24 hours. The mixture was transferred to a separatory funnel where the organic phase was separated from the aqueous phase. The organic phase was rotovapped and the ionic liquid product (i.e. the trihexyltetradecylphosphonium salt of 4,4'-(1,1-dioxido-3H-2,1-benzoxathiole-3,3-diyl)bis (2-bromo-6-isopropyl-3-methylphenol) was collected.

EXAMPLE 8

Preparation of fluorescein di-trihexyltetradecylphosphonium salt

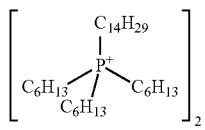

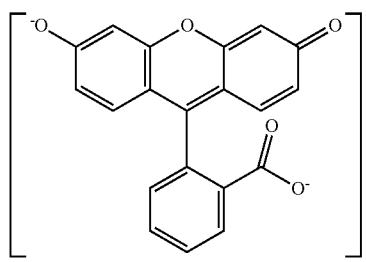

A solution of fluorescein sodium salt (2.5 grams, 6.6 millimoles) in 50 ml deionized water was prepared. A solution of trihexyltetradecylphosphonium chloride (6.88 grams, 13.3 millimoles) in 200 ml dichloromethane was also prepared. The two solutions were combined in a round bottom flask and stirred for 24 hours. The mixture was transferred to a separatory funnel where the organic phase was separated from the aqueous phase. The organic phase was then washed with 200 ml deionized water, separated from the aqueous phase, and rotovapped and the ionic liquid product (i.e. fluorescein di-trihexyltetradecylphosphonium salt) was collected.

EXAMPLE 9

Preparation of trihexyltetradecylphosphonium 2-(2, 4-Dinitrophenylazo)-1-naphthol-3,6-disulfonate

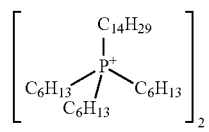

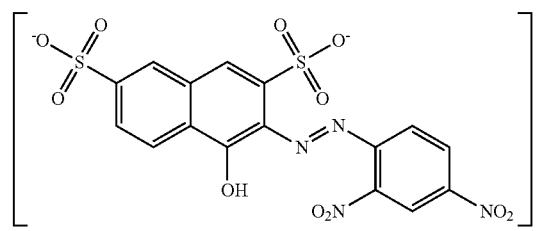

An amount of 0.43 grams (0.79 millimoles) of 2-(2,4-Dinitrophenylazo)-1-naphthol-3,6-disulfonic acid, disodium salt, otherwise known in the art as NITRAZINE YELLOW, was dissolved in 50 ml deionized water. Trihexyltetradecylphosphonium chloride (0.85 grams, 1.6 millimoles) was dissolved in 200 ml dichloromethane. The two solutions were combined into a round bottom flask and stirred for 24 hours. The mixture was transferred to a separatory funnel where the organic phase was separated from the aqueous phase. The organic phase was washed with 200 ml deionized water, separated from the aqueous phase, and rotovapped. The ionic liquid product (i.e. trihexyltetradecylphosphonium 2-(2,4-Dinitrophenylazo)-1-naphthol-3,6-disulfonate) was collected.

EXAMPLE 10

Preparation of 7-benzothiazolesulfonate acid, 2,2'-(1-triazene-1,3-diyldi-4,1-phenylene)bis(6-methyl-) di-trihexyltetradecylphosphonium salt)

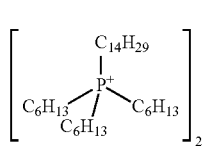 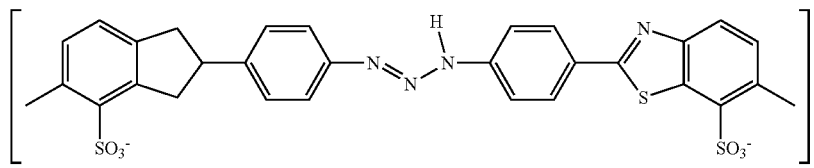

2.5 grams (3.6 millimoles) of 7-benzothiazolesulfonic acid, 2,2'-(1-triazene-1,3-diyldi-4,1-phenylene)bis(6-methyl-, disodium salt), otherwise known in the art as THIAZOLE YELLOW, was dissolved in 200 deionized water. Trihexyltetradecylphosphonium chloride (4.0 grams, 7.7 millimoles) was dissolved in 200 ml dichloromethane. The two solutions were combined into a round bottom flask and stirred for 24 hours. The mixture was transferred to a separatory funnel where the organic phase was separated from the aqueous phase. The organic phase was washed with 200 ml deionized water. The organic phase was separated and rotovapped, leaving the ionic liquid product, i.e. 7-benzothiazolesulfonate acid, 2,2'-(1-triazene-1,3-diyldi-4,1-phenylene)bis(6-methyl-)di-trihexyltetradecylphosphonium salt, which was collected.

EXAMPLE 11

Preparation of: 4,5-dihydroxy-3-(p-nitrophenylazo)-2,7-naphthalenedisulfonic acid, di-trihexyltetradecylphosphonium salt

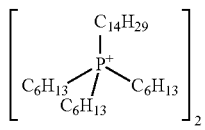

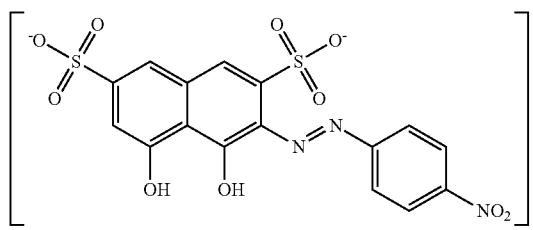

2.0 grams (3.8 millimoles) of 4,5-dihydroxy-3-(p-nitrophenylazo)-2,7-naphthalenedisulfonic acid, disodium salt, otherwise known in the art as CHROMOTROPE B, was dissolved in 100 ml deionized water. Trihexyltetradecylphosphonium chloride (4.0 grams, 7.7 millimoles) was dissolved in 100 ml dichloromethane. The two solutions were combined into a round bottom flask and stirred for 24 hours. The mixture was transferred to a separatory funnel where the organic phase was separated from the aqueous phase. The organic phase was washed with 200 ml deionized water. The organic phase was separated and rotovapped. The ionic liquid product (i.e. 4,5-dihydroxy-3-(p-nitrophenylazo)-2,7-naphthalenedisulfonic acid, di-trihexyltetradecylphosphonium salt) was collected.

EXAMPLE 12

Preparation of N-[6-(diethylamino)-9-(2,4-disulfophenyl)-3H-xanthen-3-ylidene]-N-ethyl-ethanaminium, inner salt, trihexyltetradecylphosphonium salt

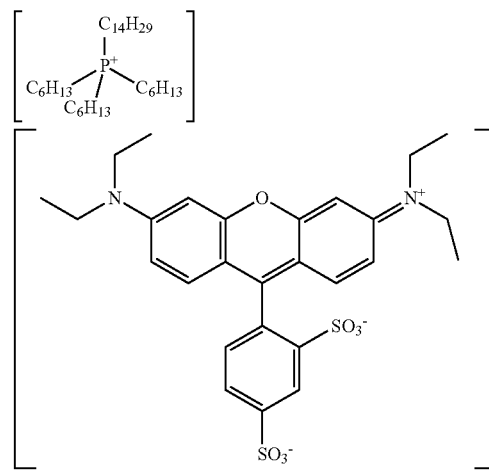

4.0 grams (6.9 millimoles) of N-[6-(diethylamino)-9-(2,4-disulfophenyl)-3H-xanthen-3-ylidene]-N-ethyl-ethanaminium hydroxide, inner salt, trihexyltetradecylphosphonium salt, otherwise known in the art as SULFORHODAMINE B, or KITON RED 620, was dissolved in methanol (5 ml). Trihexyltetradecylphosphonium chloride (4.5 grams, 8.7 millimoles) was dissolved in 100 ml dichloromethane. The two solutions were combined into a round bottom flask and stirred for 24 hours. The mixture was transferred to a separatory funnel where the organic phase was separated from the aqueous phase. The organic phase was washed with 200 ml deionized water. The organic phase was separated and rotovapped. The ionic liquid product (i.e. N-[6-(diethylamino)-9-(2,4-disulfophenyl)-3H-xanthen-3-ylidene]-N-ethyl-ethanaminium, inner salt, trihexyltetradecylphosphonium salt) was collected.

Most of the phosphonium-based RTILs prepared as described above were tested for their effectiveness as MALDI matrices for a variety of soluble cationic, anionic, and neutral analytes. Matrix-assisted desorption laser-ionization ("MALDI) mass spectrometry was performed on a 4800 PLUS MALDI-TOF system (APPLIED BIOSYSTEMS, Framingham, Mass.) in both positive ion (fixed laser intensity of 3700 arbitrary units) and negative ion (fixed laser intensity of 4300) modes using 400 shots per spectrum and with the final detector voltage set at 1.818 kV. The ionic liquid was diluted 1:10,000 in methanol because spotting the neat liquid directly on the MALDI plate led to an overabundance of signal. After dilution, 1 microliter was spotted on an OPTI TOF 384-well MALDI plate (AB SCIEX, Foster City, Calif.) such that 25 picomoles of analyte and 1 micromole of ionic liquid were distributed to each spot. The results summarized below in Table 1 include data for trihexyltetradecylphosphonium chloride (1), trihexyltetradecylphosphonium 2,5-dihydroxybenzoate (2) (Example 1) trihexyltetradecylphosphonium α-cyano-4-hydroxycinnamate (3) (Example 2), and trihexyltetradecylphosphonium ferulate (4) (Example 3).

TABLE 1

| analyte | signal in (1) | signal in (2) | signal in (3) | signal in (4) | signal, no matrix | $\lambda_{max}$ in nm | absorption at 337 |
|---|---|---|---|---|---|---|---|
| malachite green | yes | yes | yes | n.d. | yes | 618 | yes |
| Nile blue | yes | yes | n.d. | yes | n.d. | 634 | no |
| Nile red | yes | yes | yes | yes | n.d. | 521 | no |
| fluorescein | yes | yes | n.d. | n.d. | n.d. | 488 | no |
| bromothymol blue | yes | yes | weak | n.d. | n.d. | 430 | yes |
| kiton red | yes | yes | no | yes | weak | 566 | no |
| hexadecyltrimethylammonium bromide | yes | yes | yes | n.d. | no | 211 | no |
| dodecylsulfate | weak | yes | yes | yes | no | <250 | no |

Analytes malachite green, nile blue, nile red, fluorescein, bromothymol blue, kiton red, hexadecyltrimethylammonium bromide, and dodecylsulfate are listed in the first column. Whether MALDI signals were obtained for the four phosphonium-based RTILS trihexyltetradecylphosphonium chloride (1), trihexyltetradecylphosphonium 2,5-dihydroxybenzoate (2), trihexyltetradecylphosphonium α-cyano-4-hydroxycinamate (3), and trihexyltetradecylphosphonium ferulate (4) are indicated in columns 2, 3, 4, and 5, respectively. Column 6 provides data for $\lambda_{max}$ in nm for the analyte dye in water at pH of 7. All entries were performed in water except for nile red (1:1 water:ethanol) and hexadecyltrimethylammonium bromide (methanol). Column 7 summarizes whether or not there was a significant absorption of the analyte dye at 337 nanometers, which is the wavelength of the MALDI laser. A signature was deemed observable if the signal-to-noise ratio for the peak was greater than 10. The signal is marked as "weak" in the table if the signal-to-noise ratio for the peak was between 2 and 10. A signal marked as unobservable had a signal-to-noise ratio of less than 2. The peak intensity could be increased by increasing the laser intensity. The chosen laser intensity of 3700/4300 arbitrary units for the positive/negative modes resulted in a relatively low signal for some analytes in some matrices, but prevented detector saturation for the cases where ionization was high. In all samples containing $PR_4$ cation, a single peak at m/z=483.5 attributable to $PR_4$ cation was found in the positive mode. In the negative mode, a peak at 160.8 was found. No other peaks due to $PR_4$ cation were observed. Thus, the spectra were clean relative to spectra obtained with known solid MALDI matrices.

The RTILs showed strong peaks for [M−H] by MALDI in the negative mode, which corresponded to the molecular weights. The absence of contaminating unreacted acid was indicated by the lack of corresponding $[M+H]^+$ and $[M+Na]^+$ peaks which would have been expected had there been unreacted acid mixed into the RTIL.

The phosphonium-based RTILs prepared as described in Examples 4-8, 10, and 12 above was evaluated as a MALDI matrix by spotting one microliter ("uL") of a 1:10,000 dilution of the compound in methanol and measuring signal in the positive and negative modes. The presence and number of peaks was indicative of the potential use of the compound as a matrix for MALDI. The appearance of signals demonstrated that the compound could be detected by MALDI. Table 2 summarizes the results.

TABLE 2

| Example | Number of peaks in positive mode | Number of peaks in negative mode | Suitable as matrix |
|---|---|---|---|
| 4 | 1 | 6 | yes |
| 5 | 1 | 7 | yes |
| 6 | 1 | 4 | yes |
| 7 | 1 | 5 | yes |
| 8 | 1 | 3 | yes |
| 10 | 2 | 5 | yes |
| 12 | 1 | 2 | yes |

As Table 2 shows, each of the phosphonium-based RTILS of Examples 4-8, 10, and 12 are suitable as a matrix for MALDI mass spectrometry. The RTILs of Examples 9 and 11 were not tested, but are expected to also be suitable materials for a MALDI matrix.

Decomposition temperatures ($T_{dec}$) for trihexyltetradecylphosphonium 2,5-dihydroxybenzoate (2) (Example 1), trihexyltetradecylphosphonium α-cyano-4-hydroxycinnamate (3) (Example 2), and trihexyltetradecylphosphonium ferulate (4) (Example 3) were measured by thermogravimetric analysis ("TGA") under an atmosphere of nitrogen gas and are reported as the onset of weight loss with a heating rate of 10° C. per minute. Glass transition temperatures ("$T_g$") were obtained by low-temperature differential scanning calorimetry (DSC) and are reported as the onset of the transition with a heating rate of 10° C. per minute. Viscosity was measured on 1 milliliter samples with a VISCOLAB 3000 viscometer (CAMBRIDGE VISCOSITY). Samples were heated to 90° C. and viscosity was recorded at 90° C., 80° C., 70° C., and 60° C. after a 30 minute equilibration at each temperature. Thermogravimetric analysis (TGA) was performed under $N_2$ atmosphere over a temperature range of 20-500° C. with a ramp rate of 10° C. per minute and a sample size of 40 milligrams. Differential scanning calorimetry ("DSC") was performed under $N_2$ atmosphere over a temperature range of −200 to 100° C. with a ramp rate of 10° C. per minute and a sample size of 10 milligrams. Viscosities were measured at 90° C., 80° C., 70° C., and 60° C. The viscosities at 50° C. were too large to be measured using our system. Because Arrhenius plots of the data were not satisfactorily fit with the two-parameter exponential model, the viscosities were modeled with the Volger-Tammann-Fulcher (VTF) formula, shown below:

$$\ln \eta = \ln A + \left( \frac{B}{T - T_g} \right)$$

where A is the frequency factor, B is the activation energy, and Tg is the thermodynamic glass transition temperature. The three-parameter fits to this model are in Table 3 below. The second entry recites data for the anion [X] "dtc" is diethylthiocarbamate, and the numbers for dtc are taken from Fraser et al., Chem. Commun., 2007, pp. 3817-3819, incorporated by reference. The first entry recites data for the RTIL with chloride anion, and the numbers for $T_g$, $T_{dec}$, and viscosity were taken from product literature from CYTEC for the RTIL CYPHOS 101 (i.e. trihexyltetradecylphosphonium chloride).

TABLE 3

| [X] | FW (g/mol) | $T_g$ (° C. onset) | $T_{dec}$ (° C. onset) | viscosity at 60° C. ($\eta$, cP) | B (K) | A | B | $\lambda_{max}$ |
|---|---|---|---|---|---|---|---|---|
| Cl– | 519.3091 | −56 | 350 | 132.0 | 1357 | 0.0351 | 0.999 | 231 |
| dtc | 631.5319 | −77 | 255 | 1470 | 1531 | 0.0271 | 0.999 | 305 |
| DHB | 636.9683 | 55 | 288 | 1438 | 1336 | 0.0883 | 0.999 | 328 |
| CHCA | 672.0156 | −27 | 254 | 13570 | 2103 | 0.0169 | 0.999 | 327 |
| FA | 677.0321 | −58 | 244 | 1415 | 1315 | 0.998 | 0.998 | 323 |

As the data in Table 3 show, embodiment ionic liquids have viscosities that range from 1415 to 13570 cP at 60° C. These viscosities compare well with the viscosities of other $PR_4$-based ionic liquids (see, for example: Del Sesto et al, J. Organomet. Chem., 2005, vol. 690, pp. 2536-2542). Viscosities of the embodiment RTILs were all higher than the viscosity of trihexyltetradecylphosphonium chloride (i.e. CYPHOS 101). There was no apparent relationship between viscosity and anion size. The onset glass transition temperatures were also higher than that of trihexyltetradecylphosphonium chloride but below 0° C., which reflects the slow flowing nature of these materials. Trihexyltetradecylphosphonium α-cyano-4-hydroxycinnamate and trihexyltetradecylphosphonium ferulate are both liquids at room temperature. Trihexyltetradecylphosphonium 2,5-dihydroxybenzoate is a waxy solid at room temperature, but melts at 55° C. and therefore is also a RTIL (RTILs are liquids with a melting temperature below 100° C.).

The decomposition temperatures were lower for the embodiment RTILs than for trihexyltetradecylphosphonium chloride (decomposition onset at 288, 254, and 350° C. for the DHB, CHCA, and Cl salts respectively), possibly due to the instability of carboxylate groups on the anions. FTIR data collected from the TGA efflux confirm the loss of $CO_2$ at the temperatures corresponding to the onset of decomposition for each RTIL. These compare favorably with onset decomposition temperatures for alkylimidazolium and tetraalkylammonium ionic liquids.

Another aspect of the invention relates to a kit for preparing a sample of a soluble analyte in a matrix for analysis by matrix-assisted laser desorption ionization mass spectrometry. The kit includes a compound of the formula $[PR_4]_m[X]_n$ wherein m is 1 or 2, and wherein n is 1. Each R is a group that comprises 4-22 carbons and is independently selected from alkyl, alkenyl, alkynyl, phenyl, and aryl. X is an anion selected from 2,5-dihydroxybenzoate, α-cyano-4-hydroxycinnamate, ferulate, and a dye anion selected from

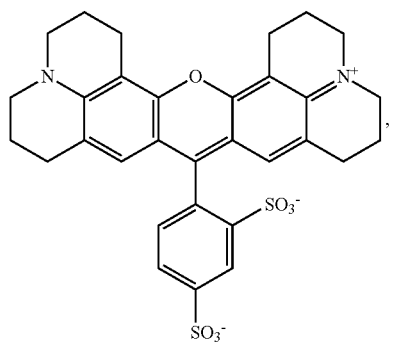

-continued

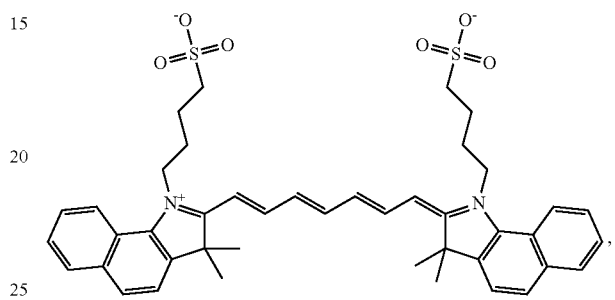

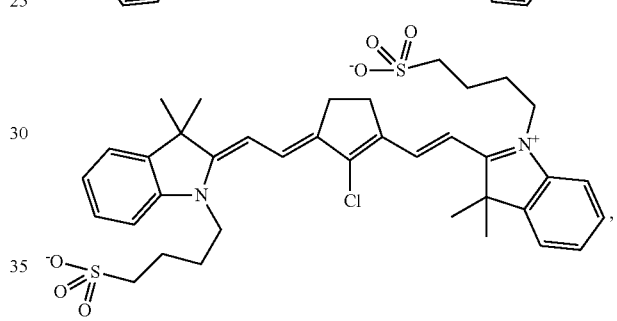

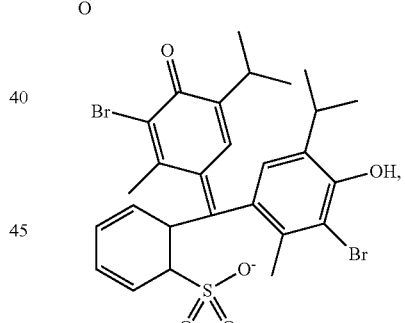

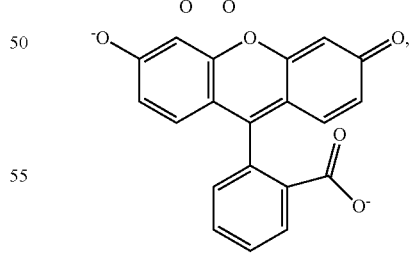

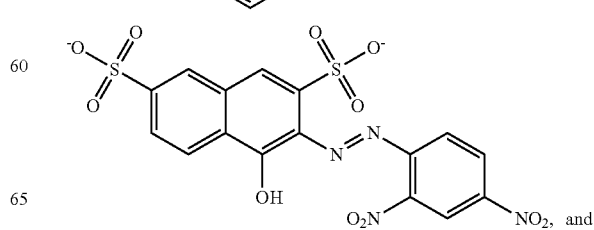

and

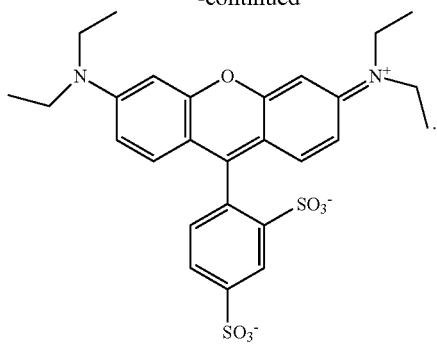

The kit also includes instructions for preparing a sample of a soluble analyte in a matrix for analysis by matrix-assisted laser desorption ionization mass spectrometry, wherein the compound is the matrix for the soluble analyte.

Another aspect of the invention involves using phosphonium-based ionic liquids and nitrogen-based ionic liquids in forensic analysis of dyes attached to keratinous substrates. Keratinous substances include, but are not limited to, wool, hoof, and feather keratin. Wool is a particularly difficult material for forensic examination because of its resistance to dissolution and the affinity with which wool dyes are bound to wool keratin. Current forensic methods of isolating dyes from wool are either ineffective or result in modification or degradation of the dye because of the high pH of the isolation conditions. In an aspect of this invention, a phosphonium-based RTIL is employed for denaturing a keratinous substrate that includes wool, hoof, and/or feather keratin, or some other keratinous substrate. The method uses RTILs to treat these substances for the purpose of obtaining forensic dye samples. According to the method of treating keratinous substrates with dyes attached to the keratinous substrates, a composition of the formula $[A]_m[X]_n$ is provided. A is a cation, X is an anion, m is 1 or 2, and n is 1. The keratinous substrate is exposed to the composition under conditions wherein the keratin is denatured, thereby separating the dye from the substrate. In the formula $[A]_m[X]_n$, A is selected from dialkylpyrrolidinium, branched dialkylpyrrolidinium, dialkylimidazolium, branched dialkylimidazolium, guanidinium, 1,1,3,3-tetraalkylguanidininum, urea, 1,1,3,3-tetraalkylurea, ammonium, trialkylammonium (such as diisopropylethylammonium), tetraalkylammonium, trialkylsulfonium, pyridinium, diphenyliodonium, 2,2,6,6-tetraalkylpiperidine, 2,2,6,6-tetraalkyl-4-piperidone, 2,2,6,6-tetraalkylpiperidinol, quinuclidinium, or may be $PR_4$ wherein each R comprises 4-22 carbons and each R is independently selected from linear alkyl, branched alkyl, cycloalkyl, phenyl, linear alkenyl, branched alkenyl, cycloalkenyl, linear alkynyl, and branched alkynyl. Examples of suitable anions (i.e. X) include, but are not limited to, halides (such as chloride, bromide, and iodide), hydroxide, acetate, anions of amino acids (such as lysine or tyrosine), tetrafluoroborate, dicyanamide, bis(trifluoromethanesulfonyl)amide, tosylate, carboxylate, phosphinate, dialkylphosphate, phosphate, methylcarbonate, decanoate, 2-ethylhexanoate, bis(2,4,4-trimethylpentyl) phosphinate, dodecylsulfonate, methanesulfonate, glycolate, diisobutylmonothiophosphate, diisobutyldithiophosphate, benzoate, tridecylsulfosuccinate, alkylsulfate, 2,5-dihydroxybenzoate, α-cyano-4-hydroxycinnamate, ferulate, sinapate, succinate, 2-(4-hydroxyphenylazo)benzoate, caffeate, nicotinate, anthranilate, trans-3-indoleacrylate, picolinate, and 3-hydroxypicolinate.

In an embodiment, keratin from swine hooves was denatured and solubilized by drying 0.2 grams of keratin from swine hooves for 16 hours at 80° C. and then treating the dried keratin with one gram of neat tetrabutylphosphonium chloride for 16 hours at 100° C. Fourier-transform infrared spectroscopy revealed a shift in the keratin-based "amide peak I" (C═O stretch) from 1640 cm−1 (solid keratin) to 1660 cm−1 (keratin in tetrabutylphosphonium chloride). The peak is visible with as little an amount as 2.5% keratin by weight in tetrabutylphosphonium chloride. The keratin "amide peak II) (CN stretch and N—H bend) is suppressed by solubilizing in tetrabutylphosphonium chloride and shifted slightly to higher wavenumbers.

In another embodiment, dye was separated from wool keratin by treating 0.2 grams of dyed wool with 1 milliliter of neat tetrabutylphosphonium hydroxide for 4 hours at 50° C. After treatment, the mixture was filtered and the filtrate was washed with 2×1 milliliter water. The dye remained in the ionic liquid phase and was analyzed by MALDI mass spectrometry as described previously. A slight increase in the UV absorption at 280 nm suggested that protein was also present in the ionic liquid. This embodiment is the most appealing for separating dye from a keratinous substrate because all of the steps of the process are performed in a single ionic liquid. Additionally, only a small amount of protein is extracted into the ionic liquid, so the water-ionic liquid interface is clean and both the water and the ionic liquid phases are sufficiently optically clear for dye analysis by UV-Vis spectroscopy.

In another embodiment, a keratinous substrate with attached dye was denatured by treating 0.2 grams of dyed wool with 1 milliliter of 0.75 M sodium hydroxide for 4 hours at 50° C. After treatment, 1 milliliter of water was added, the mixture was filtered to remove partially degraded wool, and the filtrate was extracted with 2 milliliters of trihexyltetradecylphosphonium chloride. The dye remained in the ionic liquid phase and was analyzed by MALDI as described previously. Protein co-extraction into the ionic liquid was clearly evident by strong absorption of UV light at 280 nm and, upon contacting a portion of the ionic liquid layer with 0.1 M HCl, by eye due to extensive protein precipitation.

In another embodiment, a dye was separated from a keratinous substrate by treating 0.2 grams of dyed wool with 1 milliliter of neat tetrabutylphosphonium chloride for 4 hours at 50° C. After treatment, 4 milliliters of water were added and the mixture was filtered to remove partially degraded wool. The filtrate was extracted with 4 milliliters of trihexyltetradecylphosphonium chloride and the dye was extracted into the trihexyltetradecylphosphonium layer and was analyzed by MALDI as described previously. A slight increase in the absorption of UV light at 280 nm suggested that protein was co-extracted into the ionic liquid.

In another embodiment, a dye was separated from a keratinous substrate by treating 0.2 grams of dyed wool with 1 milliliter of neat tetrabutylphosphonium L-lysate for 4 hours at 50° C. After treatment, 4 milliliters of water were added and the mixture was filtered to remove partially degraded wool. The filtrate was extracted with 4 milliliters of trihexyltetradecylphosphonium chloride and the dye was extracted into the trihexyltetradecylphosphonium layer and was analyzed by MALDI as described previously. A slight increase in the UV absorption at 280 nm suggested protein co-extracted into the ionic liquid.

In yet another embodiment, a dye was separated from a keratinous substrate by treating 0.2 grams of dyed wool with 1 milliliter of methanol for 16 hours at 30° C. After treatment, the now decolored wool was removed from the dye solution and washed with 2×1 milliliter methanol. The washes were added to the dye solution and methanol was evaporated. No evidence of protein was seen in the dye-containing residue by UV-Vis spectroscopy or by Fourier-transform infrared spectroscopy. The dye-containing residue was redissolved in 2 mL water and extracted with trihexyltetradecylphosphonium chloride. The dye was extracted into the ionic liquid layer and was analyzed by MALDI as described previously.

Another aspect of the invention relates to a more general preparation of a dye-containing sample for analysis. In this more general process, a solution of analyte is provided. Also provided is a composition of the formula $[PR_4]_m[X]_n$ wherein m is 1-2 and n is 1. Each R comprises 4-22 carbons and each R is independently selected from alkyl, alkenyl, and alkynyl. X is an anion. Suitable anions include chloride, bromide, iodide, hydroxide, acetate, an anionic dye, tetrafluoroborate, dicyanamide, bis(trifluoromethanesulfonyl)amide, tosylate, carboxylate, phosphinate, dialkylphosphate, phosphate, methylcarbonate, decanoate, 2-ethylhexanoate, bis(2,4,4-trimethylpentyl)phosphinate, dodecylsulfonate, methanesulfonate, glycolate, diisobutylmonothiophosphate, diisobutyldithiophosphate, benzoate, tridecylsulfosuccinate, alkylsulfate, 2,5-dihydroxybenzoate, α-cyano-4-hydroxycinnamate, ferulate, sinapate, succinate, 2-(4-hydroxyphenylazo)benzoate, caffeate, nicotinate, anthranilate, trans-3-indoleacrylate, picolinate, or 3-hydroxypicolinate. According to the method, a solution of dye is contacted with the composition, resulting in extraction of dye from the solution into the composition, resulting in preparation of a sample of the dye in the ionic liquid. The sample of dye can then be analyzed by a technique such as, but not limited to, MALDI mass spectrometry.

To demonstrate the method, a variety of solutions of dyes were prepared. Aqueous solutions of anionic, cationic, and neutral dyes were prepared as 5 milllimolar ("mM") solutions in 1 milliliter ("mL") of water. NILE RED was prepared as a 2.5 mM solution in 2 mL of a 1:1 water:ethanol mixture. Based on the extinction coefficient, the dyes were diluted to 15 micromolar (malachite green, fluorescein, kiton red) or 250 micromolar (nile blue, nile red, bromothymol blue) in 2 milliliters of water at room temperature.

For experiments in which pH was controlled, the ionic liquid was conditioned prior to use in the dye extraction.

In an embodiment extraction procedure, a 2 mL portion of neat trihexyltetradecylphosphonium chloride was added to an aqueous solution of a dye, resulting in a two-layered sample that was shaken vigorously. The sample was centrifuged to 200 rpm (515×g) for 30 minutes in a THERMO IEC CENTRA CL2 centrifuge equipped with 4-hole fixed angle rotor (part number 804SF) to obtain a clean separation of the ionic liquid and aqueous layers. The layers were separated from each other. Each layer was separately centrifuged for 1 minute at 1000 rpm (130×g) to improve clarity. Absorbance over a range from 200 to 900 nanometers was quantified using an HP 8453 UV-Visible Spectrophotometer. The pH of the aqueous layer before and after extraction was determined for all samples.

Trihexyltetradecylphosphonium chloride was used for dye extraction. Forensic samples are generally small. Therefore, the dyes must be efficiently extracted from the forensic samples. Extraction efficiencies were determined according to the formula $$E\% = \frac{C_i - C_f}{C_i}.$$

$C_i$ and $C_f$ are the initial and final molar concentrations of the dye in the aqueous layer, respectively. Partition constants were determined according to the formula $$P_{IL,aq} = C_{A,IL}/C_{A,aq}$$

which is the ratio of concentration of an analyte 'A' extracted into the ionic liquid phase to the concentration of 'A' in the aqueous phase after extraction. Six dyes were used to demonstrate dye extraction using trihexyltetradecylphosphonium chloride. The results are shown in Table 4 below. The first column lists the dyes: malachite green, nile blue, nile red, fluorescein, bromothymol blue, and kiton red. Aqueous solutions of the dyes were prepared. The starting pH of each of the solutions was between 7.0 and 7.5. The second, third, and fourth column show the extraction efficiencies at no control of pH (column 2) at a pH of 7 (column 3), and at a pH of 10 (column 4). The partition coefficients are given in column 5 at pH of 7. The charges of the dyes at pH 2, 7.5, and 10 are provided in columns 6, 7, and 8, respectively.

TABLE 4

| dye | extraction efficiency, no pH control | extraction efficiency at pH 7 | extract. eff. (pH 10) | part. coeff. (pH 7) | charge at pH 2 | charge at pH 7.5 | charge at pH 10 |
| --- | --- | --- | --- | --- | --- | --- | --- |
| Malachite green | 99.97% | n.d. | n.d. | 44 | +2 | +1 | +1 |
| Nile blue | 74.14% | 87.29% | n.d. | 7 | +1 | +1 | 0 |
| Nile red | 76.27% | 99.37% | n.d. | 157 | 0 | 0 | 0 |
| fluorescein | 92.07% | 97.94% | n.d. | 48 | +1 | −2 | −2 |
| Bromothymol blue | 0.00% | 0.00% | 100.00% | n.d. | 0 | −1 | −1 |
| Kiton red | 98.31% | 99.86% | n.d. | 730 | −1 | −1 | −1 |

Conditioning of the ionic liquids may involve washing the ionic liquid once with 0.1 M sodium bicarbonate and thrice with water. For example, trihexyltetradecylphosphonium chloride (i.e. CYPHOS101) was conditioned by washing once with 0.1 M sodium bicarbonate and thrice with water, which raised the pH of the aqueous layer to 7.5. Extractions containing bromothymol blue were additionally performed from ionic liquid conditioned to pH=10 using 0.5 M sodium hydroxide.

Anionic dyes were extracted with the highest efficiency in the $PR_4$-based ionic liquids. A possible explanation for this is that a metathesis-type reaction involving an exchange of chloride ion and dye anion is occurring, resulting in the formation of a small percentage of dye-based ionic liquid. Cationic dyes were also extracted, although at reduced efficiency relative to anionic dyes. The concentration of dye in the ionic liquid was very low (a maximum concentration of 0.25 mM).

Data collected for dyes dissolved in $PR_4$-based RTILs were compared to data for the dyes dissolved in methanol. For kiton red, an anionic dye, ionization in the negative mode was better with $[PR_4][Cl]$, $[PR_4][DHB]$, and $[PR_4][FA]$ matrices than for a matrix of solid DHB. Dodecylsulfate did not ionize well with solid DHB but did ionize with $[PR_4][DHB]$, $[PR_4][CHCA]$, $[PR_4][FA]$, and, to a lesser degree, with $[PR_4][Cl]$.

Better ionization was observed using malachite green, nile blue, or hexadecyltrimethylammonium cation in the positive mode with solid DHB in methanol than with any of $[PR_4][Cl]$, $[PR_4][DHB]$, and $[PR_4][CHCA]$. The neutral dye analyzed was the lipophilic stain NILE RED; ionization of NILE RED was much stronger in the solid matrices than in any of the phosphonium-based ionic liquids.

The anionic dyes tended to ionize significantly better in the $PR_4$-based RTILs than in solid matrices. Most wool dyes are anionic. Therefore, the process of this invention related to analysis of dyes attached to keratinous substrates, which uses phosphonium-based RTILs as matrices, is much more effective than a process employing solid matrices.

Nucleic acids and oligonucleotides, like most wool dyes, are anionic materials. It is expected that a phosphonium-based ionic liquid matrix of the present invention would be an excellent matrix for analysis of nucleic acids and nucleotides by MALDI mass spectrometry. It is expected that a phosphonium-based ionic liquid matrix of the present invention would be a better matrix for analysis of nucleic acid and nucleotides by MALDI mass spectrometry than a solid matrix (such as a matrix of solid matrix of 3-hydroxypicolinic acid).

Water-immiscible trihexyltetradecylphosphonium chloride was used to extract anionic, neutral, and cationic, water-soluble dyes from aqueous solutions into the ionic liquid in a two phase system. After control of the pH of the extraction system, anionic dyes were extracted with the highest efficiency (98 to 100%), and neutral and cationic dyes were also extracted with high efficiency (87 to 99%). For the analytic dye concentrations studied, charge balancing ions in the form of protons from water in the ionic liquid or hydroxide/chloride are likely ion-exchange partners facilitating the extraction. A significant drop in the pH of water in the presence of trihexyltetradecylphosphonium chloride was investigated and found to correlate with the presence of chloride ions in the aqueous phase, suggesting that hydroxide ion readily substitutes for chloride in trihexyltetradecylphosphonium chloride. Analysis of dyes was achieved using trihexyltetradecylphosphonium 2,5-dihydroxybenzoate, trihexyltetradecylphosphonium α-cyano-4-hydroxycinnamate, and trihexyltetradecylphosphonium ferulate. Peaks for analytes in these RTILs compared favorably with peaks observed in trihexyltetradecylphosphonium chloride and also in traditional solid MALDI matrices in methanol. The phosphonium-based matrices tended to ionize anions better than the traditional MALDI matrices do, but they do not ionize cations as well as the traditional solid MALDI matrices do.

In summary, phosphonium-based RTILs were synthesized and used as matrices for matrix-assisted laser desorption ionization (MALDI) mass spectrometry. A method for extraction of dyes from keratinous substrates and from aqueous solutions using the RTILs was developed. $PR_4$-based RTILs of this invention are useful for the separation of dyes from fabrics, extraction of dyes from aqueous solution, and identification of the dyes by MALDI. $PR_4$-based RTILs are suitable for analysis of anionic analytes by MALDI. The use of $PR_4$-based RTIL matrices for MALDI mass spectrometry suggests that the present process may be applied in forensic analysis, drug detection, and wastewater treatment processes.

Although the present invention has been described with reference to specific details, it is not intended that such details should be regarded as limitations upon the scope of the invention, except as and to the extent that they are included in the accompanying claims.

What is claimed is:

1. A matrix for matrix-assisted laser desorption ionization mass spectrometry, said matrix comprising a composition of the formula $[PR_4]_m[X]_n$, said composition being a molten salt with a melting temperature below 100° C., wherein m is 1 or 2 and n is 1, wherein each R is a group that comprises 4-22 carbons and is independently selected from alkyl, alkenyl, alkynyl, phenyl, and aryl, wherein X is an anion selected from 2,5-dihydroxybenzoate, α-cyano-4-hydroxycinnamate, ferulate, and a dye anion selected from

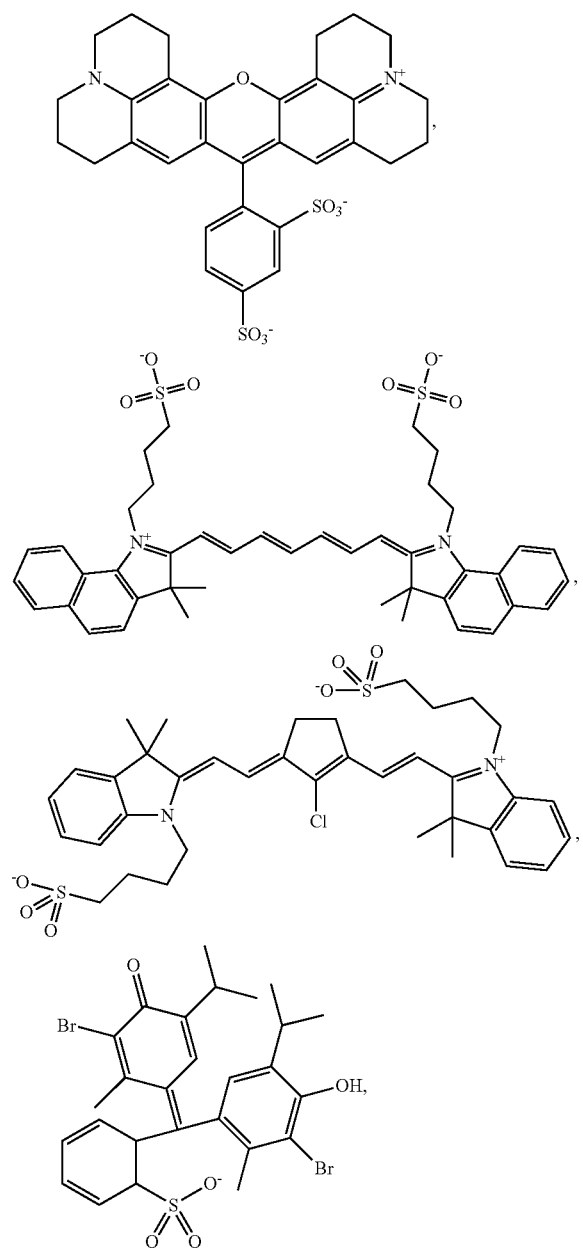

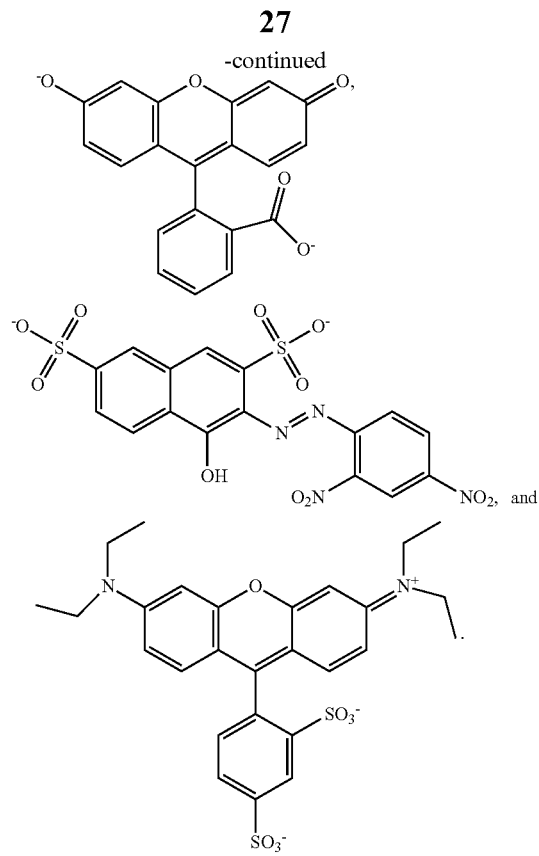

2. A matrix for matrix-assisted laser desorption ionization mass spectrometry, said matrix comprising a composition of the formula $[PR_4]_m[X]_n$, said composition being a molten salt with a melting temperature below 100° C., wherein m is 1 or 2 and n is 1, wherein $[PR_4]$ is selected from trihexyltetradecylphosphonium, triisobutyl(methyl)phosphonium, tributyl(methyl)phosphonium, tributyl(hexadecyl)phosphonium, tetrabutylphosphonium, tetraoctylphosphonium, tetradecyl(tributyl)phosphonium, ethyl(tributyl)phosphonium), tributyl(methyl)phosphonium, triisobutyl(methyl)phosphonium, triisobutyl(ethyl)phosphonium, triethyl(methoxyethyl)phosphonium, tri(isobutyl)methylphosphonium, triethyl[2-(2-methoxyethoxy)ethyl]phosphonium, tetraphenylphosphonium, butyltriphenylphosphonium, trihexylmethylphosphonium, and trihexyl(ethyl)phosphonium, wherein X is an anion selected from 2,5-dihydroxybenzoate, α-cyano-4-hydroxycinnamate, ferulate, and a and a dye anion selected from

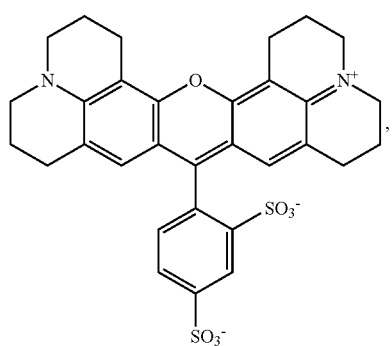

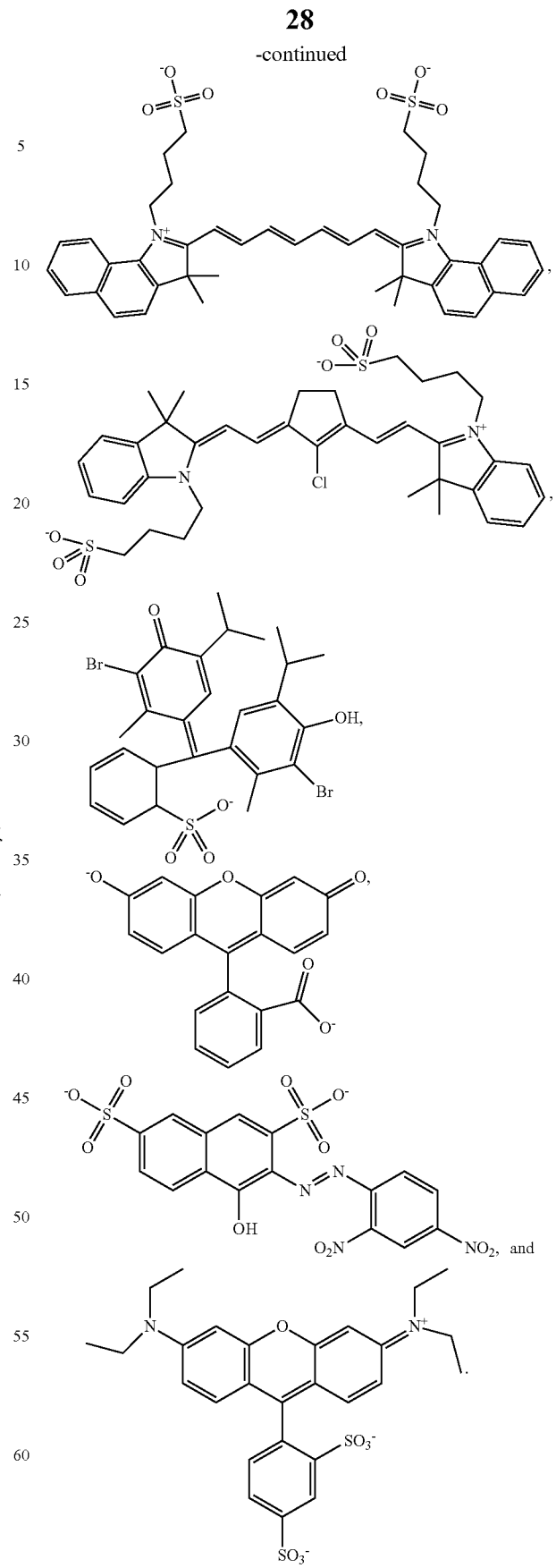

3. The matrix of claim 1, wherein $[PR_4]$ is trihexyltetradecylphosphonium.

4. A kit for preparing a sample of a soluble analyte in a matrix for analysis by matrix-assisted laser desorption ionization mass spectrometry, said kit comprising a compound of the formula $[PR_4]_m[X]_n$ wherein m is 1 or 2, wherein n is 1, and wherein each R is a group that comprises 4-22 carbons and is independently selected from alkyl, alkenyl, alkynyl, phenyl, and aryl, wherein X is an anion selected from 2,5-dihydroxybenzoate, α-cyano-4-hydroxycinnamate, ferulate, and a dye anion, the dye anion selected from

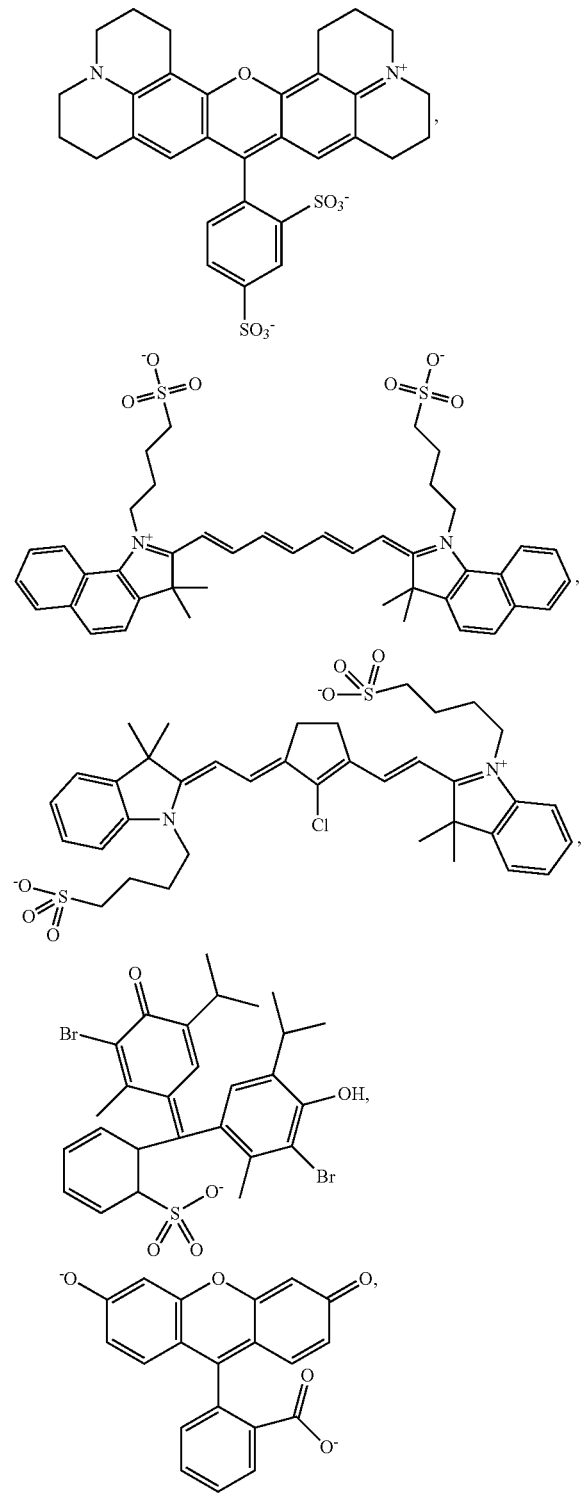

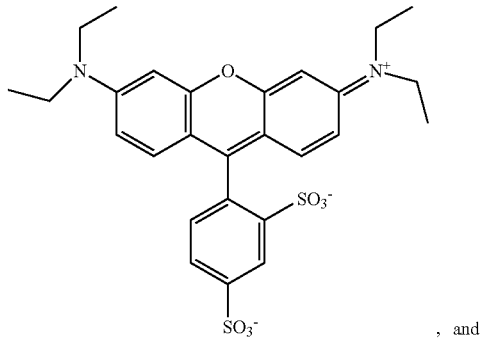

, and

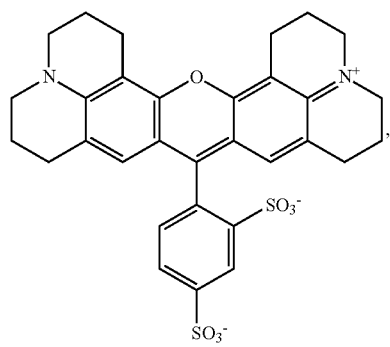

, and instructions for preparing a sample of a soluble analyte in a matrix for analysis by matrix-assisted laser desorption ionization mass spectrometry, wherein said compound is the matrix for the soluble analyte.

5. A kit for preparing a sample of a soluble analyte in a matrix for analysis by matrix-assisted laser desorption ionization mass spectrometry, said kit comprising a compound of the formula $[PR_4]_m[X]_n$ wherein m is 1 or 2 wherein n is 1 and wherein $[PR_4]$ is selected from trihexyltetradecylphosphonium, triisobutyl(methyl)phosphonium, tributyl(methyl) phosphonium, tributyl(hexadecyl)phosphonium, tetrabutylphosphonium, tetraoctylphosphonium, tetradecyl (tributyl)phosphonium, ethyl(tributyl)phosphonium), tributyl(methyl)phosphonium, triisobutyl(methyl)phosphonium, triisobutyl(ethyl)phosphonium, triethyl(methoxyethyl)phosphonium, tri(isobutyl)methylphosphonium, triethyl[2-(2-methoxyethoxy)ethyl]phosphonium, tetraphenylphosphonium, butyltriphenylphosphonium, trihexylmethylphosphonium, and trihexyl(ethyl)phosphonium, wherein X is an anion selected from 2,5-dihydroxybenzoate, α-cyano-4-hydroxycinnamate, ferulate, and a dye anion, the dye anion selected from -continued

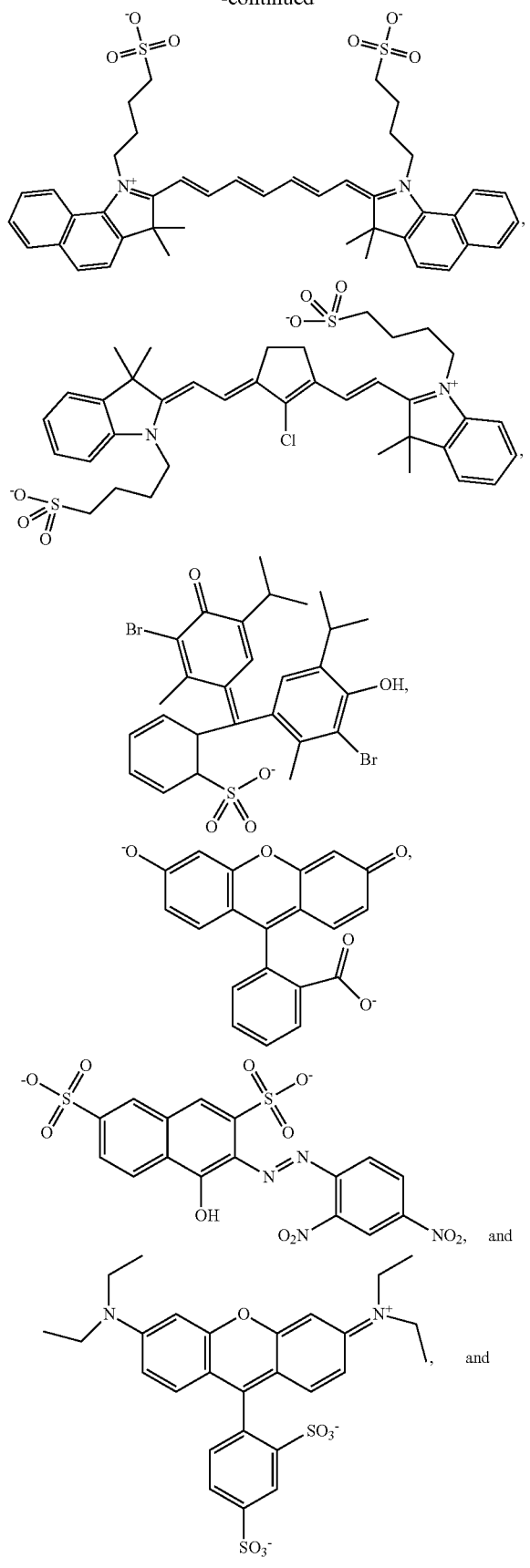

instructions for preparing a sample of a soluble analyte in a matrix for analysis by matrix-assisted laser desorption ionization mass spectrometry, wherein said compound is the matrix for the soluble analyte.

6. The kit of claim 4, wherein $PR_4$ is trihexyltetradecylphosphonium.

7. A composition of the formula $[PR_4]_m[X]_n$ wherein m is 1 or 2, wherein n is 1, wherein each R is a group that comprises 4-22 carbons and is independently selected from alkyl, alkenyl, alkynyl, phenyl, and aryl, wherein X is an anion selected from 2,5-dihydroxybenzoate, α-cyano-4-hydroxycinnamate, ferulate, and a dye anion, the dye anion selected from

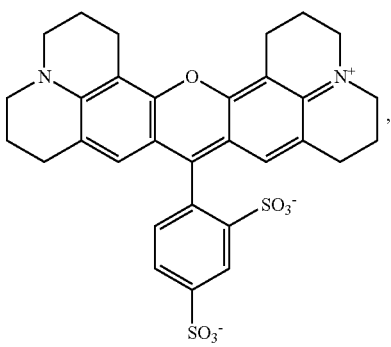

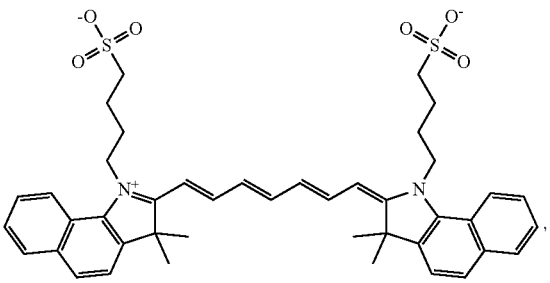

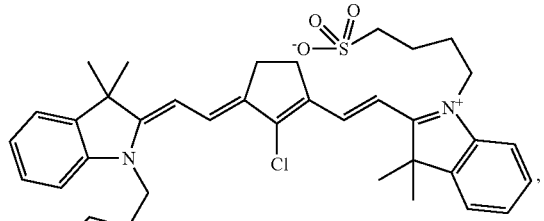

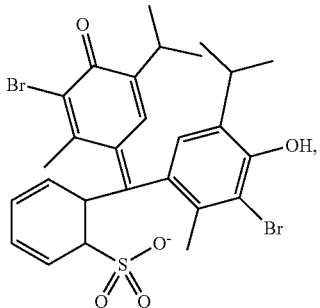

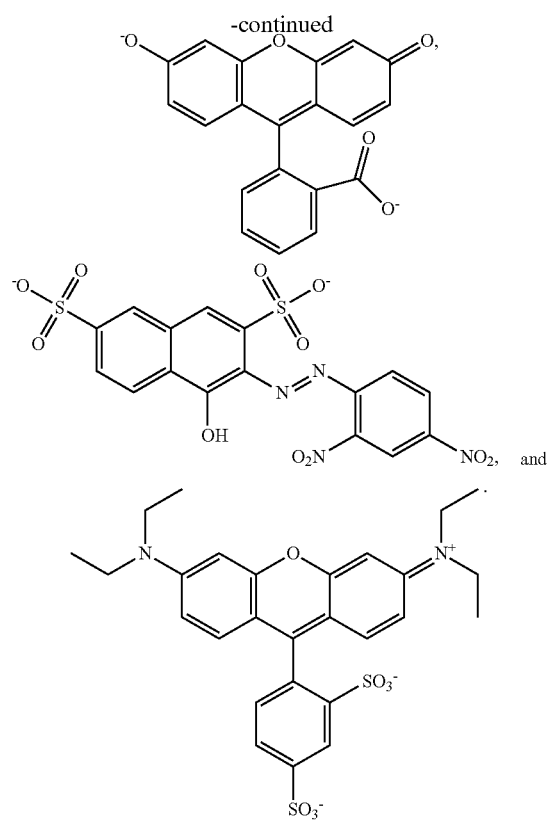

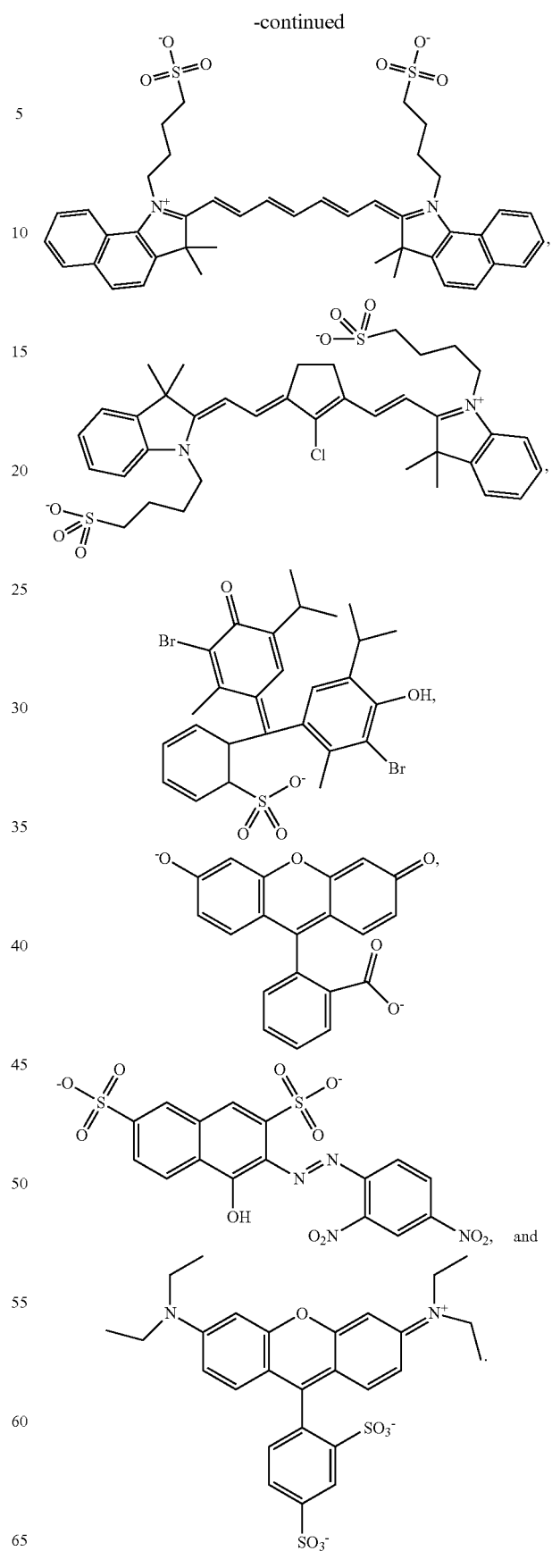

8. A composition of the formula [PR$_4$]$_m$[X]$_n$ (wherein m is 1 or 2, wherein n is 1, wherein [PR$_4$] is selected from trihexyltetradecylphosphonium, triisobutyl(methyl)phosphonium, tributyl(methyl)phosphonium, tributyl(hexadecyl)phosphonium, tetrabutylphosphonium, tetraoctylphosphonium, tetradecyl(tributyl)phosphonium, ethyl(tributyl)phosphonium), tributyl(methyl)phosphonium, triisobutyl(methyl)phosphonium, triisobutyl(ethyl)phosphonium, triethyl(methoxyethyl)phosphonium, tri(isobutyl)methylphosphonium, triethyl[2-(2-methoxyethoxy)ethyl]phosphonium, tetraphenylphosphonium, butyltriphenylphosphonium, trihexylmethylphosphonium, and trihexyl(ethyl)phosphonium, wherein X is an anion selected from 2,5-dihydroxybenzoate, α-cyano-4-hydroxycinnamate, ferulate, and a dye anion, the dye anion selected from

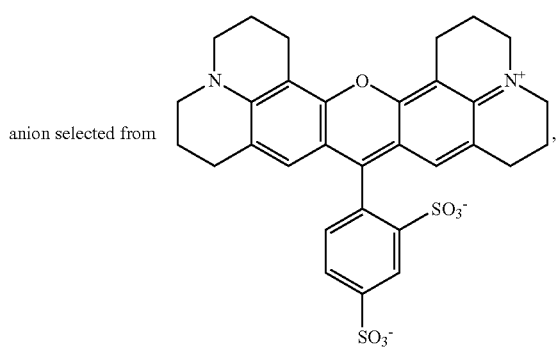

9. The composition of claim 7, wherein $PR_4$ is trihexyltetradecylphosphonium.

10. A composition of the formula $[PR_4]_m[X]_n$ wherein m is 1 or 2, wherein n is 1, wherein each R is a group that comprises 4-22 carbons, wherein each R is independently selected from linear alkyl, branched alkyl, cycloalkyl, linear alkenyl, branched alkenyl, cycloalkenyl, phenyl, aryl, linear alkynyl, and branched alkynyl, wherein X is selected from all-trans-retinoate, iodate, anthraquinone-2-carboxylate, 7-hydroxycoumarinyl-4-acetate, aurintricarboxylate, 3,6-dihydroxyflavone, 9-hydroxy-9-fluorenecarboxylate, 2-(4-hydroxyphenylazo)benzoate, mellitate, 2,3-napthalenedicarboxylate, curcuminate, sinapate, succinate, 2-(4-hydroxyphenylazo)benzoate, caffeate (3,4-dihydroxycinnamate), nicotinate, anthranilate, trans-3-indoleacrylate, picolinate, or 3-hydroxypicolinate, said composition having a melting temperature of less than 100° C.

* * * * *